(12) United States Patent
Crank

(10) Patent No.: US 7,641,621 B2
(45) Date of Patent: Jan. 5, 2010

(54) ELONGATED INTRA-LUMENAL MEDICAL DEVICE

(75) Inventor: Justin M. Crank, Saint Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1359 days.

(21) Appl. No.: 10/647,613

(22) Filed: Aug. 25, 2003

(65) Prior Publication Data

US 2005/0049523 A1 Mar. 3, 2005

(51) Int. Cl.
*A61B 5/00* (2006.01)
*A61M 25/00* (2006.01)

(52) U.S. Cl. ..................................... 600/585
(58) Field of Classification Search .................. 600/585
See application file for complete search history.

(56) References Cited

U.S. PATENT DOCUMENTS

| | | | |
|---|---|---|---|
| 3,174,851 A | | 3/1965 | Buehler et al. |
| 3,351,463 A | | 11/1967 | Rozner et al. |
| 3,753,700 A | | 8/1973 | Harrison et al. |
| 3,973,556 A | | 8/1976 | Fleischhacker et al. |
| 4,003,369 A | * | 1/1977 | Heilman et al. ............. 600/585 |
| 4,080,706 A | | 3/1978 | Heilman et al. |
| 4,724,846 A | * | 2/1988 | Evans, III ................... 600/585 |
| 5,052,404 A | | 10/1991 | Hodgson |
| 5,107,852 A | | 4/1992 | Davidson et al. |
| 5,144,959 A | * | 9/1992 | Gambale et al. ............. 600/585 |
| 5,211,183 A | | 5/1993 | Wilson |
| 5,213,111 A | | 5/1993 | Cook et al. |
| 5,238,004 A | | 8/1993 | Sahatjian et al. |
| 5,373,619 A | | 12/1994 | Fleischhacker, Jr. et al. |
| 5,409,015 A | | 4/1995 | Palermo |
| 5,437,288 A | | 8/1995 | Schwartz et al. |
| 5,452,726 A | | 9/1995 | Burmeister et al. |
| 5,465,732 A | | 11/1995 | Abele |
| 5,477,856 A | | 12/1995 | Lundquist |

(Continued)

FOREIGN PATENT DOCUMENTS

| | | |
|---|---|---|
| DE | 198 23 414 A1 | 6/1999 |
| GB | 13017 | 0/1910 |
| WO | 98/58697 A1 | 12/1998 |
| WO | WO 01/10350 A1 | 2/2001 |

OTHER PUBLICATIONS

U.S. Appl. No. 10/346,698, filed Jan. 17, 2003, Miller et al.

*Primary Examiner*—Max Hindenburg
*Assistant Examiner*—Jeffrey G Hoekstra
(74) *Attorney, Agent, or Firm*—Crompton, Seager & Tufte, LLC

(57) ABSTRACT

A medical device includes a coil having a longitudinal axis and a radial axis orthogonal to the longitudinal axis, formed from a wire. The wire includes a cross-section with a centroid, a moment of inertia with respect to an axis running through the centroid and parallel to the longitudinal axis of the coil, and a moment of inertia with respect to an axis running through the centroid and parallel to the radial axis of the coil. The moment of inertia with respect to an axis running through the centroid and parallel to the longitudinal axis of the coil is greater than the moment of inertia with respect to an axis running through the centroid and parallel to the radial axis of the coil.

18 Claims, 4 Drawing Sheets

U.S. PATENT DOCUMENTS

| | | |
|---|---|---|
| 5,573,520 A | 11/1996 | Schwartz et al. |
| 5,722,424 A | 3/1998 | Engelson |
| 5,724,989 A * | 3/1998 | Dobson .................. 600/585 |
| 5,741,429 A | 4/1998 | Donadio, III et al. |
| 5,746,701 A | 5/1998 | Noone |
| 5,749,837 A | 5/1998 | Palermo et al. |
| 5,769,796 A * | 6/1998 | Palermo et al. ............ 600/585 |
| 5,772,609 A * | 6/1998 | Nguyen et al. ............. 600/585 |
| 5,797,857 A | 8/1998 | Obitsu |
| 5,827,201 A * | 10/1998 | Samson et al. ............. 600/585 |
| 5,836,893 A | 11/1998 | Urick |
| 5,924,998 A | 7/1999 | Cornelius et al. |
| 5,951,494 A | 9/1999 | Wang et al. |
| 5,957,865 A | 9/1999 | Foote et al. |
| 6,001,068 A | 12/1999 | Uchino et al. |
| 6,019,736 A | 2/2000 | Avellanet et al. |
| 6,056,702 A * | 5/2000 | Lorenzo .................. 600/585 |
| 6,059,771 A | 5/2000 | Balbierz et al. |
| 6,139,510 A | 10/2000 | Palermo |
| 6,139,511 A | 10/2000 | Huter et al. |
| 6,165,140 A | 12/2000 | Ferrera |
| 6,165,292 A | 12/2000 | Abrams et al. |
| 6,171,338 B1 | 1/2001 | Talja et al. |
| 6,329,069 B1 | 12/2001 | Azizi et al. |
| 6,368,316 B1 | 4/2002 | Jansen et al. |
| 6,379,369 B1 | 4/2002 | Abrams et al. |
| 6,428,489 B1 | 8/2002 | Jacobsen et al. |
| 6,488,637 B1 | 12/2002 | Eder et al. |
| 6,508,803 B1 | 1/2003 | Horikawa et al. |
| 6,544,197 B2 | 4/2003 | DeMello |
| 2002/0013540 A1 | 1/2002 | Jacobsen et al. |
| 2002/0072689 A1 | 6/2002 | Klint |
| 2003/0069520 A1 | 4/2003 | Skujins et al. |
| 2003/0069521 A1 | 4/2003 | Reynolds et al. |
| 2004/0181174 A2 | 9/2004 | Davis et al. |

\* cited by examiner

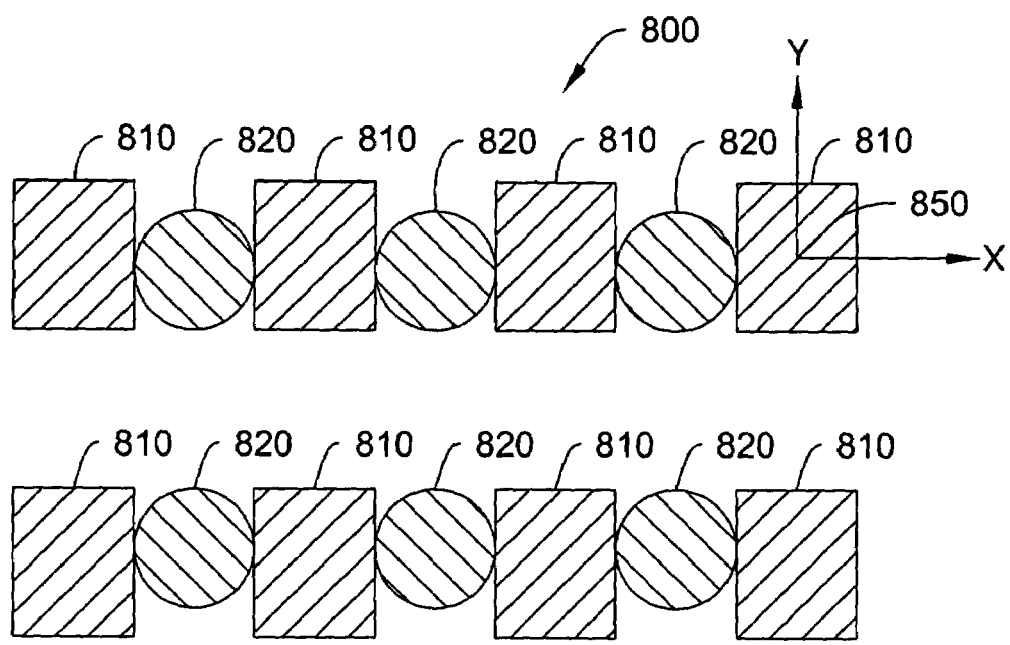
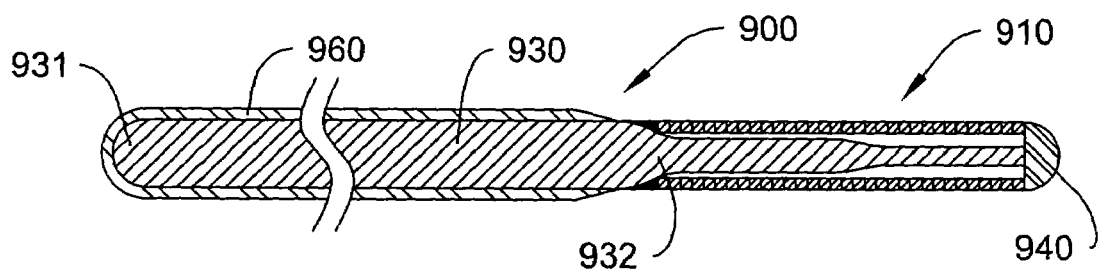
Fig.8
Fig.9

ELONGATED INTRA-LUMENAL MEDICAL DEVICE

TECHNICAL FIELD

The invention generally pertains to intra-lumenal medical devices, such as guidewires, catheters or the like, wherein in use, they are inserted into vascular lumens or other body lumens for treatment and diagnosis.

BACKGROUND

A wide variety of medical devices have been developed for intraluminal, especially intracorporeal, use. Elongated medical devices are commonly used to facilitate navigation through and/or treatment within the anatomy of a patient. Because the anatomy of a patient may be tortuous, it is desirable to combine a number of performance features in such devices. For example, it is sometimes desirable that the device have a relatively high level of pushability and torqueability, particularly near its proximal end. It is also sometimes desirable that a device be relatively flexible, particularly near its distal end. A number of different elongated medical device structures and assemblies are known, each having certain advantages and disadvantages. However, there is an ongoing need to provide alternative elongated medical device structures and assemblies.

SUMMARY

The invention provides several alternative designs, materials and methods of manufacturing alternative medical device structures and assemblies.

Accordingly, an example embodiment of the invention can be found in a medical device that includes a coil having a longitudinal axis and a radial axis orthogonal to the longitudinal axis, formed from a wire. The wire includes a cross-section with a centroid, a moment of inertia with respect to an axis running through the centroid and parallel to the longitudinal axis of the coil, and a moment of inertia with respect to an axis running through the centroid and parallel to the radial axis of the coil. The moment of inertia with respect to an axis running through the centroid and parallel to the longitudinal axis of the coil is greater than the moment of inertia with respect to an axis running through the centroid and parallel to the radial axis of the coil.

Another example embodiment of the invention can be found in a medical guidewire that includes an elongated shaft including a proximal region having a first outer diameter and a distal region having a second outer diameter that is smaller than the first outer diameter and a coil member connected to the elongated shaft at the proximal region and extending from the proximal region over the distal region. The coil member has an inner diameter that is greater than the second outer diameter. The coil has a longitudinal axis and a radial axis orthogonal to the longitudinal axis. The coil is formed from a wire that includes a cross-section with a centroid, a moment of inertia with respect to an axis running through the centroid and parallel to the longitudinal axis of the coil; and a moment of inertia with respect to an axis running through the centroid and parallel to the radial axis of the coil. The moment of inertia with respect to an axis running through the centroid and parallel to the longitudinal axis of the coil is greater than the moment of inertia with respect to an axis running through the centroid and parallel to the radial axis of the coil.

Another example embodiment of the invention can be found in a medical device that includes a coil having a longitudinal axis and a radial axis orthogonal to the longitudinal axis. The coil is formed from a composite wire that includes a cross-section with a centroid, a wire longitudinal axis parallel to the coil longitudinal axis and a wire radial axis parallel to the coil radial axis, a first material having a first Young's Modulus at the centroid, and a second material having a second Young's Modulus further away from the centroid along the wire radial axis. The second Young's Modulus is greater than the first Young's Modulus.

Another example embodiment of the invention can be found in a medical guidewire that includes an elongated shaft including a proximal region having a first outer diameter and a distal region having a second outer diameter that is smaller than the first outer diameter. A coil member is connected to the elongated shaft at the proximal region and extending from the proximal region over the distal region. The coil member has an inner diameter that is greater than the second outer diameter. The coil has a longitudinal axis and a radial axis orthogonal to the longitudinal axis. The coil is formed from a composite wire that includes a cross-section with a centroid, a wire longitudinal axis parallel to the coil longitudinal axis and a wire radial axis parallel to the coil radial axis, a first material having a first Young's Modulus at the centroid, and a second material having a second Young's Modulus further away from the centroid along the wire radial axis. The second Young's Modulus is greater than the first Young's Modulus.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 8 is a cross-sectional view of an example coil co-wound with a second coil;

FIG. 9 is a cross-sectional view of an example guidewire with a coil;

Figure 1:
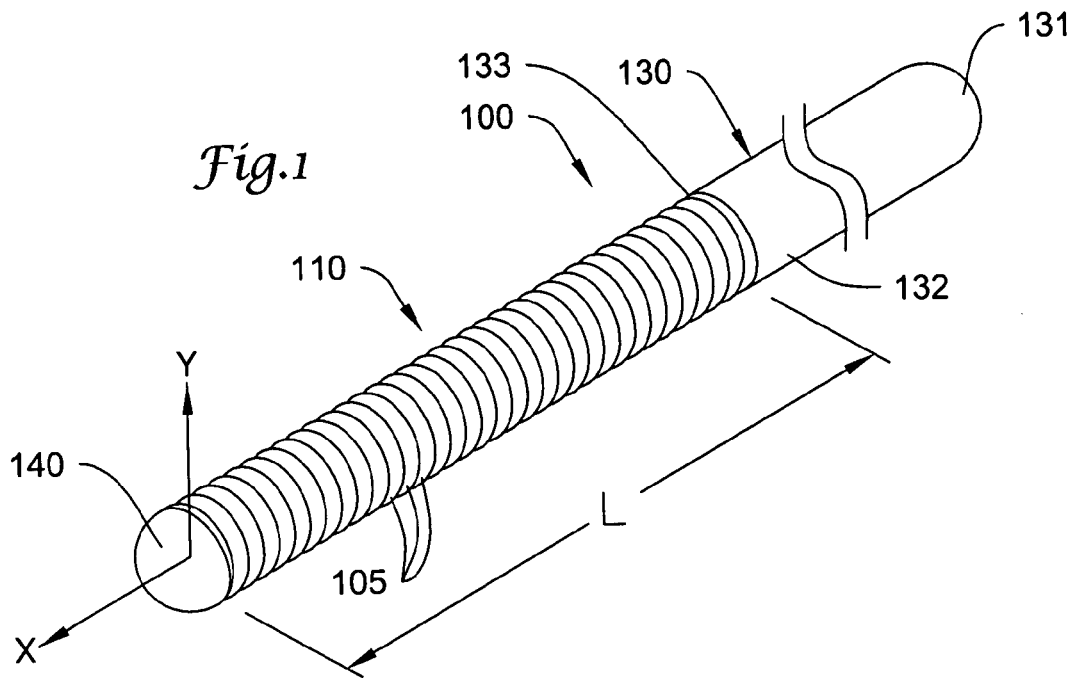
FIG. 1 is a perspective view of an example coil, incorporated into an elongate medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF PREFERRED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention. For example, although discussed with specific reference to guidewires in the particular embodiments described herein, the invention may be applicable to a variety of medical devices that are adapted to be advanced into the anatomy of a patient through an opening or lumen. For example, the invention may be applicable to fixed wire devices, catheters (e.g., guide, balloon, stent delivery, etc.), drive shafts for rotational devices such as atherectomy catheters and IVUS catheters, endoscopic devices, laproscopic devices, embolic protection devices, spinal or cranial navigational devices, and other such devices. Additionally, while some embodiments may be adapted or configured for use within the vasculature of a patient, other embodiments may be adapted and/or configured for use in other anatomies. It is to be understood that a broad variety of materials, dimensions and structures can be used to construct suitable embodiments, depending on the desired characteristics. The following examples of some embodiments are included by way of example only, and are not intended to be limiting.

Refer now to FIG. 1, which is a perspective view of a coil 110, incorporated into an elongate medical device 100. The elongate medical device 100 may include an elongate shaft or core 130. The elongate shaft or core 130 can have a proximal end 131 and an opposing distal end 132. The coil 110 can be disposed on a portion of the elongate shaft, for example, at the distal end 132. A distal tip 140 can be disposed on an end of the coil 110 and/or the elongate shaft or core 130. The coil 110 may have a plurality of windings 105 that form a coil length L.

The coil 110 can be formed of a variety of materials including metals, metal alloys, polymers, and the like. Some examples of material for use in the coil 110 include a metal or a metal alloy such as a stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof.

Further examples of suitable alloys include silver-cadmium alloy, gold-cadmium alloy, gold-copper-zinc alloy, copper-aluminum-nickel alloy, copper-gold-zinc alloy, copper-zinc alloy, copper-zinc-aluminum alloy, copper-zinc-tin alloy, copper-zinc-silicon alloy, iron-beryllium alloy, iron-platinum alloy, indium-thallium alloy, iron-manganese alloy, nickel-titanium-cobalt alloy, and copper-tin alloy.

Some additional examples of suitable material include a polymer material, such as, for example, a high performance polymer. The material forming the coil 110 wire may be a material with a high Poisson's ratio, such as, a value greater than 0.25 or 0.3 or 0.4 or 0.5. A material forming the wire for the coil 110 with a high Poisson's ratio can provide a coil with a higher torque-ability to flexibility ratio.

In some embodiments, the coil 110 or portions thereof can be made of, or coated or plated with, or otherwise include a radiopaque material. Radiopaque materials are understood to be materials capable of producing a relatively bright image on a fluoroscopy screen or another imaging technique during a medical procedure. This relatively bright image aids the user of medical device 100 in determining its location. Some examples of radiopaque materials can include, but are not limited to, gold, platinum, palladium, tantalum, tungsten alloy, polymer material loaded with a radiopaque filler, and the like, or combinations or alloys thereof.

Additionally, the coil 110, or other portions of the device 100, can include materials or structure to impart a degree of MRI compatibility. For example, to enhance compatibility with Magnetic Resonance Imaging (MRI) machines, it may be desirable to make the coil 110, or other portions of the medical device 100, in a manner that would impart a degree of MRI compatibility. For example, the elongate shaft or core 130, the coil 110, or portions thereof, or other portions of the device 100, may be made of a material that does not substantially distort the image and create substantial artifacts (artifacts are gaps in the image). Certain ferromagnetic materials, for example, may not be suitable because they may create artifacts in an MRI image. The elongate shaft or core 130, the coil 110, or portions thereof, may also be made from a material that the MRI machine can image. Some materials that exhibit these characteristics include, for example, tungsten, Elgiloy, MP35N, nitinol, and the like, and others, or combinations or alloys thereof. The wire that forms the coil 110 may be formed of a homogenous material or be a composite structure.

In some embodiments, the coil 110 can be made of a material that is compatible with the core wire 130 and the distal tip 140. The particular material used can be chosen in part based on the desired flexibility requirements or other desired characteristics. In some particular embodiments, the coil 110 can be formed from a superelastic or linear elastic nickel-titanium alloy, for example, linear elastic or superelastic nitinol.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). Within the family of commercially available nitinol alloys, is a category designated "super elastic" (i.e., pseudoelastic) and a category designated "linear elastic". Although these two categories of material are similar in chemistry, they each exhibit distinct and useful mechanical properties. Either, or both superelastic and linear elastic nitinol can be used.

One example of a suitable nickel-titanium alloy that may exhibit linear elastic properties is FHP-NT alloy commercially available from Furukawa Techno Material Co. of Kanagawa, Japan. Some examples of suitable nickel-titanium alloys that may exhibit linear elastic characteristics include those disclosed in U.S. Pat. Nos. 5,238,004 and 6,508,803, which are incorporated herein by reference.

The coil 110 can be formed of a wire having shapes disclosed below and ranging in dimensions to achieve the desired flexibility. It can also be appreciated that other cross-sectional shapes or combinations of shapes may be utilized without departing from the spirit of the invention. For example, the cross-sectional shape of wire used to make the coil may be a circle, oval, rectangular, square, I-Beam, triangle, polygonal, and the like, or any suitable shape as further described below.

In some embodiments, the coil 110 can be wrapped in a helical fashion by conventional winding techniques. The pitch of adjacent turns of the coil 110 may be tightly wrapped so that each turn, at least in part, touches or is in close proximity to the succeeding turn, the pitch may be set such that the coil 110 is wrapped in an open fashion, or co-wound with a second coil as further described below. The coil 110 has a longitudinal axis x, and a radial axis y orthogonal to the longitudinal axis x as indicated by coordinate axis in FIGS. 1-8. The longitudinal axis x is parallel to the length L of the coil 110.

Such a coil 110, as discussed herein, can be incorporated into a broad variety of medical devices. For example, as shown in FIG. 1, the coil 110 can be incorporated into an elongate medical device 100, such as a guidewire, that may include an elongate shaft or core 130. The coil 110 can be disposed on a portion of the elongate shaft, for example, proximate the distal end 132. It should be understood, however, that such a coil can be incorporated into a broad variety of medical devices.

With reference to the embodiment shown in FIG. 1, the elongate shaft or core 130 can have a solid cross-section or a hollow cross-section. In other embodiments, the elongate shaft or core 130 can include a combination of areas having solid cross-sections and hollow cross sections. Moreover, the elongate shaft or core 130 can be made of rounded wire, flattened ribbon, or other such structures having various cross-sectional geometries. The cross-sectional geometries along the length of the elongate shaft or core 130 can also be constant or can vary. For example, FIG. 1 depicts the elongate shaft or core 130 as having a generally round cross-sectional shape. It can be appreciated that other cross-sectional shapes or combinations of shapes may be utilized without departing from the spirit of the invention. For example, the cross-sectional shape of the elongate shaft or core 130 may be oval, rectangular, square, polygonal, and the like, or any suitable shape.

In some embodiments, the elongate shaft or core 130 can be formed of any suitable metallic, polymeric or composite material. In some embodiments, part or all of the elongate shaft or core 130 can be formed of a metal or a metal alloy such as stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof.

Further examples of suitable alloys include silver-cadmium alloy, gold-cadmium alloy, gold-copper-zinc alloy, copper-aluminum-nickel alloy, copper-gold-zinc alloy, copper-zinc alloy, copper-zinc-aluminum alloy, copper-zinc-tin alloy, copper-zinc-silicon alloy, iron-beryllium alloy, iron-platinum alloy, indium-thallium alloy, iron-manganese alloy, nickel-titanium-cobalt alloy, and copper-tin alloy.

The particular material used can be chosen in part based on the desired flexibility requirements or other desired characteristics or the elongate shaft or core 130. In some particular embodiments, the elongate shaft or core 130 can be formed from a superelastic or linear elastic nickel-titanium alloy, for example, those discussed above with regard to the coil 110.

The entire elongate shaft or core 130 can be made of the same material, or in some embodiments, can include portions or sections that are made of different materials. In some embodiments, the material used to construct different portions of the core wire 130 can be chosen to impart varying flexibility and stiffness characteristics to different portions of the wire. For example, a proximal portion 131 and a distal portion 132 can be formed of different materials (i.e., materials having different moduli of elasticity) resulting in a difference in flexibility. In some embodiments, the material used to construct the proximal portion 131 can be relatively stiff for push-ability and torque-ability, and the material used to construct the distal portion 132 can be relatively flexible by comparison for better lateral track-ability and steer-ability. To illustrate, the proximal portion 131 can be formed of, for example, straightened 304v stainless steel wire, and the distal portion 130 can be formed of, for example, a straightened super elastic or linear elastic alloy (e.g., nickel-titanium) wire.

In embodiments where different portions of elongate shaft or core 130 are made of different material, the different portions can be connected using any suitable connecting techniques. For example, the different portions of the elongate shaft or core 130 can be connected using welding, soldering, brazing, adhesive, or the like, or combinations thereof. Additionally, some embodiments can include one or more mechanical connectors or connector assemblies to connect the different portions of the elongate shaft or core 130 that are made of different materials The connector may include any structure generally suitable for connecting portions of an elongate shaft or core 130 One example of a suitable structure includes a structure such as a hypotube or a coiled wire which has an inside diameter sized appropriately to receive and connect the different portions of the elongate shaft or core 130. Some methods and structures that can be used to interconnect different shaft sections are disclosed in U.S. patent application Ser. Nos 09/972,276, and 10/086,992, which are incorporated herein by reference.

In some embodiments, portions or all of the elongate shaft or core 130, the coil 110, or other structures included within the medical device 100 may also be doped with, coated or plated with, made of, or otherwise include a radiopaque material. Additionally, in some embodiments, a degree of MRI compatibility can be imparted into the medical device 100, as discussed above.

The elongate shaft or core 130 may include one or more tapers or tapered regions. The tapered regions may be linearly tapered, tapered in a curvilinear fashion, uniformly tapered, non-uniformly tapered, or tapered in a step-wise fashion. The angle of any such tapers can vary, depending upon the desired flexibility and torque transmission characteristics. The length of the taper may be selected to obtain a more (longer length) or less (shorter length) gradual transition in stiffness. It can be appreciated that essentially any portion of the elongate shaft or core 130 may be tapered and the taper can be in either the proximal or the distal direction. The number, arrangement, size, and length of the tapering and constant diameter portions can be varied to achieve the desired characteristics, such as flexibility and torque transmission characteristics.

The distal tip 140 can be formed from a variety of different materials, depending on desired performance characteristics. In some embodiments, the distal tip can form an a traumatic portion on the distal end of the device 100. In some embodiments, the distal tip 140 can be formed of a material such as a metallic material that is amenable to being welded, soldered, or otherwise attached to the distal end 132 of the elongate shaft or core 130. For example, in some embodiments, the distal tip 140 can be a solder tip that is disposed via soldering at the distal end of the device and forms an a traumatic rounded portion. In other embodiments, the distal tip can be a prefabricated, or partially prefabricated, structure that is thereafter attached to the distal end of the device using suitable attachment techniques, such as welding, soldering, brazing, crimping, friction fitting, adhesive bonding, mechanical interlocking and the like. A variety of different processes, such as soldering, deep drawing, roll forming or metal stamping, metal injection molding, casting and the like, can be used to form the distal tip 140.

In some embodiments, it may be beneficial, but not always necessary, that the distal tip 140 to be formed of a material that is compatible with the particular joining technique used to connect the tip 140 to the other structure. For example, in some particular embodiments, it can be beneficial but not necessary for the distal tip 140 to be formed of the same metal or metal alloy as the distal end 132 of the elongate shaft or core 130. For example, if the elongate shaft or core 130 is formed of stainless steel, it can be beneficial for the distal tip 140 to be formed of stainless steel. In other embodiments, both of the distal tip 140 and the distal end 132 of the elongate shaft or core 130 can be formed of the same metal alloy, such as nitinol.

To form the assembly 100 shown in FIG. 1, the coil 110 can be disposed over the elongate shaft or core 130 as illustrated. The coil 110 can be secured to the elongate shaft or core 130 in any suitable manner, including for example welding, soldering, brazing, crimping, friction fitting, adhesive bonding, mechanical interlocking and the like. In the embodiment shown, the coil 110 can be secured at its proximal end to the elongate shaft or core 130 at a proximal attachment point 133, and can be secured at its distal end to the elongate shaft or core 130 via the distal tip 140. In some embodiments, the distal tip 140 is a solder tip or a weld tip that is soldered or welded to the elongate shaft or core 130 and the coil 110, and forms an atraumatic tip. In other embodiments, the distal tip 140 is prefabricated, or partially prefabricated, and is connected to the elongate shaft or core 130 and the coil 110 using a suitable attachment technique.

In some embodiments, the coil 110 and/or the distal tip can be welded to the elongate shaft or core 130. It is to be appreciated that various welding processes can be utilized without deviating from the spirit and scope of the invention. In general, welding refers to a process in which two materials such as metal or metal alloys are joined together by heating the two materials sufficiently to at least partially melt adjoining surfaces of each material. A variety of heat sources can be used to melt the adjoining materials. Examples of welding processes that can be suitable in some embodiments include LASER welding, resistance welding, TIG welding, microplasma welding, electron beam, and friction or inertia welding.

LASER welding equipment that may be suitable in some embodiments is commercially available from Unitek Miyachi of Monrovia, Calif. and Rofin-Sinar Incorporated of Plymouth, Mich. Resistance welding equipment that may be useful in some embodiments is commercially available from Palomar Products Incorporated of Carlsbad, Calif. and Polaris Electronics of Olathe, Kans. TIG welding equipment that may be useful in some embodiments is commercially available from Weidiogic Incorporated of Newbury Park, Calif. Microplasma welding equipment that may be useful in some embodiments is commercially available from Process Welding Systems Incorporated of Smyrna, Tenn.

In some embodiments, laser or plasma welding can be used to secure the distal tip 140, the coil 110 and the elongate shaft or core 130 securely together. In laser welding, a light beam is used to supply the necessary heat. Laser welding can be beneficial in the processes contemplated by the invention, as the use of a laser light heat source can provide pinpoint accuracy. In some embodiments, laser diode soldering can be useful.

It should also be understood that the device 100 can include additional structure, such as shaping ribbons, marker bands and/or coils, additional inner or outer coils, inner or outer sheaths, and the like. Those of skill in the art and others will recognize how to incorporate such additional structures into the device, as is generally known.

Figure 2:
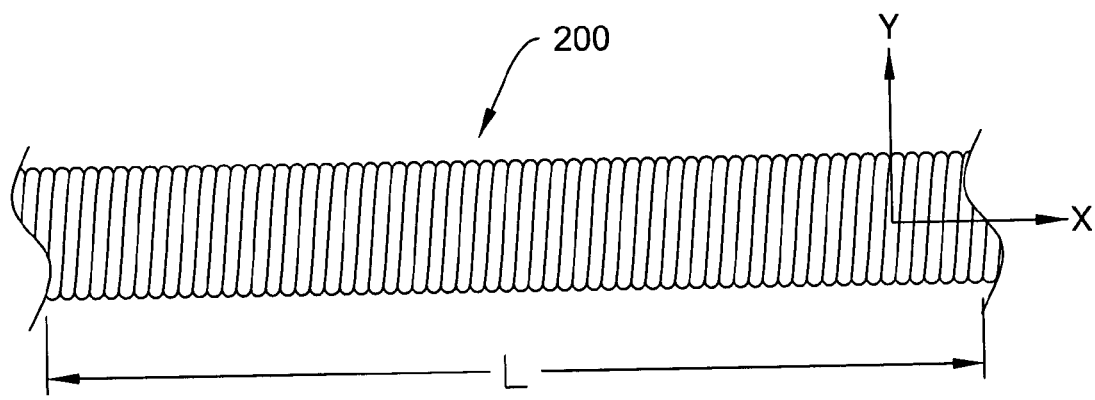
FIG. 2 is a partial side elevation view of an example medical device coil.

FIG. 2 is a partial side elevation view of another example embodiment of a coil 200 having a coil length L. The coil 200 has a longitudinal axis x, and a radial axis y orthogonal to the longitudinal axis x.

Figure 3:
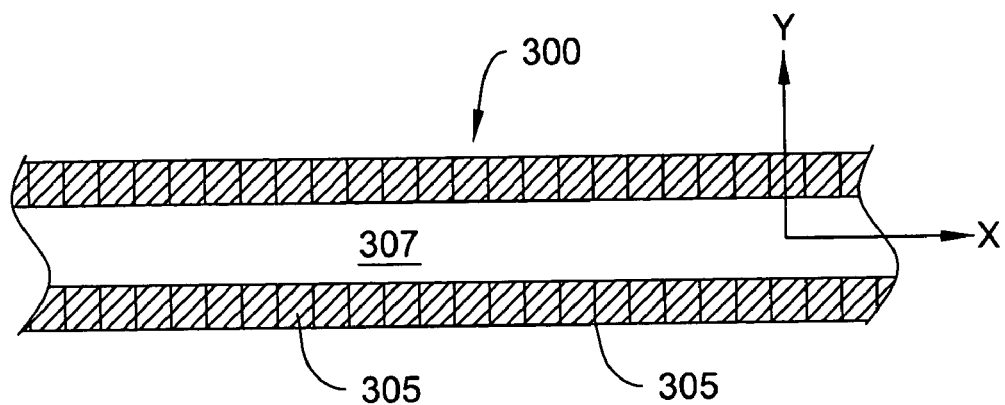
FIG. 3 is a longitudinal cross-sectional view of the example coil of FIG. 2.

FIG. 3 is a cross-sectional view of an example coil 300. The coil 300 has a longitudinal axis x, and a radial axis y orthogonal to the longitudinal axis x and a lumen 307. The coil 300 is formed from a wire 305 having a cross-section. The coil 300 coordinate system can be transposed directly onto the wire 305 cross-section as described below. The wire 305 cross-section is shown as rectangular; however, the wire 305 cross-section may be any shape conforming to the limits described herein.

Figure 4:
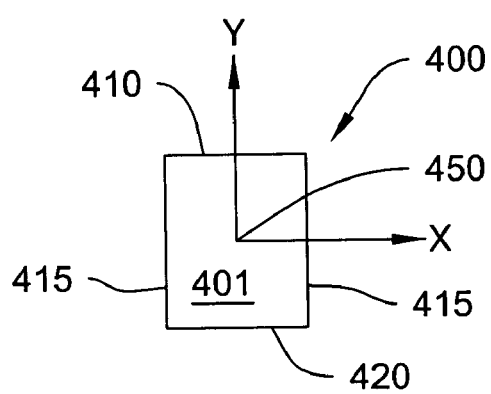
FIG. 4 is a cross-sectional view of an example wire forming a coil.

FIG. 4 is a cross-sectional view of an example wire 400 forming a coil. The wire 400 has a cross-sectional area 401 defined by an inner surface 410, an opposing outer surface 420 and parallel walls 415 connecting the inner surface 410 and the outer surface 420. The inner surface 410 defines a lumen (307) of the coil and the outer surface 420 defines an outer surface of the coil (300). The cross-sectional area 401 shown corresponds to a rectangle having longer radial walls 415 than longitudinal walls 410,420.

The cross-sectional area 401 has a centroid 450 a longitudinal axis x parallel to the coil longitudinal axis, and a radial axis y parallel to the coil radial axis and orthogonal to the longitudinal axis x. The centroid 450 may be a point which defines the geometric center of a cross-sectional surface area or object. The longitudinal axis x intersects the radial axis y at the centroid 450. The centroid 450 of any cross-sectional area or object is easily determined through basic geometric mathematics. The cross-sectional area 401 has a moment of inertia $I_x$ with respect to an axis running through the centroid 450 and parallel to the longitudinal axis x of the coil. This is also referred to as $I_x$ or the moment of inertia of a plane area with respect to the x axis. The cross-sectional area 401 has a moment of inertia $I_y$ with respect to an axis running through the centroid 450 and parallel to the radial axis y of the coil. This is also referred to as $I_y$ or the moment of inertia of a plane area with respect to the y axis. These are defined by the integrals:

$$I_x = \int y^2 dA \quad I_y = \int x^2 dA$$

in which x and y are the coordinates of the differential elements of area dA. The moment of inertia $I_x$ with respect to an axis running through the centroid 450 and parallel to the longitudinal axis x of the coil is greater than the moment of inertia $I_y$ with respect to an axis running through the centroid 450 and parallel to the radial axis y of the coil.

Figure 5:
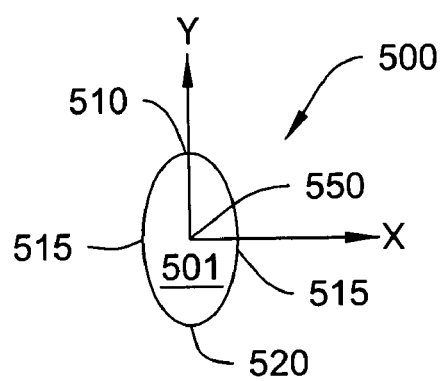
FIG. 5 is a cross-sectional view of an example wire forming a coil.

FIG. 5 is a cross-sectional view of an example wire 500 forming a coil. The wire 500 has a cross-sectional area 501 defined by an inner surface 510, an opposing outer surface 520 and curved walls 515 connecting the inner surface 510 and the outer surface 520. The inner surface 510 defines a lumen (307) of the coil and the outer surface 520 defines an outer surface of the coil (300). The cross-sectional area 501 shown corresponds to an ellipse having longer radial walls 515 than longitudinal walls 510,520.

The cross-sectional area 501 has a centroid 550 as defined above, a longitudinal axis x parallel to the coil longitudinal axis, and a radial axis y parallel to the coil radial axis and orthogonal to the longitudinal axis x. The cross-sectional area 501 has a moment of inertia $I_x$ (as defined above) with respect to an axis running through the centroid 550 and parallel to the longitudinal axis x of the coil. The cross-sectional area 501 has a moment of inertia $I_y$ (as defined above) with respect to an axis running through the centroid 550 and parallel to the radial axis y of the coil. The moment of inertia $I_x$ with respect to an axis running through the centroid 550 and parallel to the longitudinal axis x of the coil is greater than the moment of inertia $I_y$ with respect to an axis running through the centroid 550 and parallel to the radial axis y of the coil.

Figure 6:
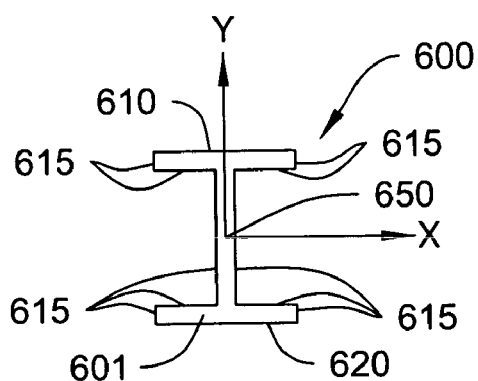
FIG. 6 is a cross-sectional view of an example wire forming a coil.

FIG. 6 is a cross-sectional view of an example wire 600 forming a coil. The wire 600 has a cross-sectional area 601 defined by an inner surface 610, an opposing outer surface 620 and walls 615 connecting the inner surface 610 and the outer surface 620. The inner surface 610 defines a lumen (307) of the coil and the outer surface 620 defines an outer surface of the coil (300). The cross-sectional area 601 shown corresponds to an I-Beam shape.

The cross-sectional area 601 has a centroid 650 as defined above, a longitudinal axis x parallel to the coil longitudinal axis, and a radial axis y parallel to the coil radial axis and orthogonal to the longitudinal axis x. The cross-sectional area 601 has a moment of inertia $I_x$ (as defined above) with respect to an axis running through the centroid 650 and parallel to the longitudinal axis x of the coil. The cross-sectional area 601 has a moment of inertia $I_y$ (as defined above) with respect to an axis running through the centroid 650 and parallel to the radial axis y of the coil. The moment of inertia $I_x$ with respect to an axis running through the centroid 650 and parallel to the longitudinal axis x of the coil is greater than the moment of inertia $I_y$ with respect to an axis running through the centroid 650 and parallel to the radial axis y of the coil.

The described wire shapes can be manufactured in a variety of ways such as, for example, extrusion, winding, 3D photo-etching, laser cutting, drawing, or the like. As will be apparent to those skilled in the art, the above-listed cross-sectional shapes are merely illustrative and various other shapes meeting the criteria set out herein may also be used in the practice of the invention.

Figure 7:
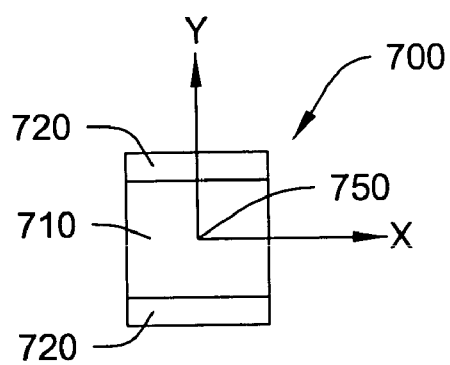
FIG. 7 is a cross-sectional view of an example wire forming a coil.

FIG. 7 is a cross-sectional view of an example composite wire 700 forming a coil. FIG. 7 is similar in shape to FIG. 4; however, FIG. 7 is an example of a composite wire 700 used to form the coil. While a rectangular shape is shown, any shape may be used such as circular or square including the shapes disclosed above to form the composite wire. A composite wire 700 can provide the features of the invention when the actual geometry of the wire is constrained to a circle or square shape.

The composite wire 700 has a centroid 750, a wire longitudinal axis x parallel to the coil longitudinal axis x and a wire radial axis y parallel to the coil radial axis y. A first material 710 having a first Young's Modulus is disposed at the centroid 750 and a second material 720 having a second Young's Modulus is disposed further away from the centroid 750 than the first material 710 along the wire radial axis y. The second material's 720 Young's Modulus is greater than the first material's 710 Young's Modulus. Thus, the second material 720 is stiffer than the first material. The second material 720 Young's Modulus may be 1% to 1000% or 10% to 500% or 20% to 300% or 20% to 200% or 20% to 100% greater than the first material 710 Young's Modulus. The second material 720 Young's Modulus may be 1%, 10%, 20%, 50%, 100%, 200%, 300%, 500%, 1000%, or 2000% greater than the first material 710 Young's Modulus. The composite wire 700 may be formed by co-extrusion for plastic composite wire 700 or by ion deposition or fusing for metallic composite wire 700.

An example of a metallic composite wire 700 may be where the first material 710 is nitinol (10 Mpsi) and the second material 710 is stainless steel (30 Mpsi). Another example of a plastic composite wire 700 may be where the first material 710 is a polyurethane (2 ksi) and the second material 710 is a poly-ether-ether-ketone (500 ksi).

The described wire shapes can be manufactured in a variety of ways such as, for example, co-extrusion, winding, 3D photo-etching, laser cutting, or the like. As will be apparent to those skilled in the art, the above-listed materials are merely illustrative and various other materials meeting the criteria set out above may also be used in the practice of the invention.

A coil-wire cross-section that moves material away from the x-axis without moving the same amount of material away from the centroid and y-axis will increase the torque-ability/flexibility ratio of the coil. Increasing the moment of inertia about the x-axis of the crass-section of the coil-wire increases the torsional rigidity of the coil. Not increasing the polar moment of inertia about the centroid of the cross-section of the coil-wire as fast makes the coil more flexible Thus, increasing the moment of inertia about the x-axis and not increasing the polar moment of inertia about the centroid as rapidly will provide a coil that efficiently transmits torque without sacrificing the flexibility of the coil The moment of inertia about the x-axis can be 1% to 1000%, 10% to 500%, 20% to 300%, 20% to 200%, 50% to 100% greater than the moment of inertia about the y-axis. The moment of inertia about the x-axis can be 1%, 5%, 10%, 20%, 30%, 40%, 50%, 75%, 100%, 200%, 300%, 500%, 1000%, or 2000% greater than the moment of inertia about the y-axis.

FIG. 8 is a cross-sectional view of an example co-wound coil 800. First coil elements 810 can be co-wound with second coil elements 820 to produce a co-wound coil 800. First coil elements 810 can have a moment of inertia $I_x$ with respect to an axis running through the centroid 850 and parallel to the longitudinal axis x of the coil being greater than a moment of inertia $I_y$ with respect to an axis running through the centroid 850 and parallel to the radial axis y of the coil. The second coil elements 820 can be any shape such as a circle or square and be made of any suitable material. The second coil elements 820 space the first coil elements 810 away from each other. This co-wound coil 800 enhances the properties of the invention while reducing pinching of the target vessel wall by the coil 800.

FIG. 9 is a cross-sectional view of the guidewire 900 with a coil 910 in accordance with the invention. The guidewire 900 includes a core 930. The core may have a proximal section 931 and an opposing distal section 932. The distal section 932 can include a series of tapered and constant diameter sections as illustrated in FIG. 9. In other embodiments, the proximal section 931 may also include a series of tapered and constant diameter sections. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. It can be appreciated that essentially any portion of guidewire 900 and/or guidewire sections 931/932 may be tapered and the taper can be in either the proximal or the distal direction. In some other embodiments, a guidewire core wire can have a profile in which the core wire has a greater number of constant diameter sections, separated by a greater number of taper sections. In some embodiments, a guidewire core wire can have fewer or no tapers. The tapers can be as illustrated in FIG. 9, or they can be longer (more gradual), or shorter (less gradual).

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire during the grinding process. Some examples of suitable grinding methods are disclosed in U.S. patent application Ser. No. 10/346,698, herein incorporated by reference. The narrowing and constant diameter portions as shown in FIG. 9 are not intended to be limiting, and alterations of this arrangement can be made without departing from the spirit of the invention. One of skill will recognize that a guidewire core wire can have a profile different from that illustrated in FIG. 9.

The coil 910 can be disposed about a portion of the core distal section 932. The core 930 can be formed from a variety of materials as described above and provide the features described above. The coil 910 can be disposed between the core 930 and a distal tip 940 and constructed as described above.

A guidewire in accordance with some embodiments of the invention can optionally include a coating layer 960 such as a lubricious coating layer over part or all of the guidewire assembly 900. Hydrophobic coatings such as fluoropolymers provide a dry lubricity which improves guide wire handling and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, the more distal portion 932 of the guidewire is coated with a hydrophilic polymer and the more proximal portion 931 is coated with a fluoropolymer 960, such as polytetrafluoroethylene (PTFE).

Figure 10:
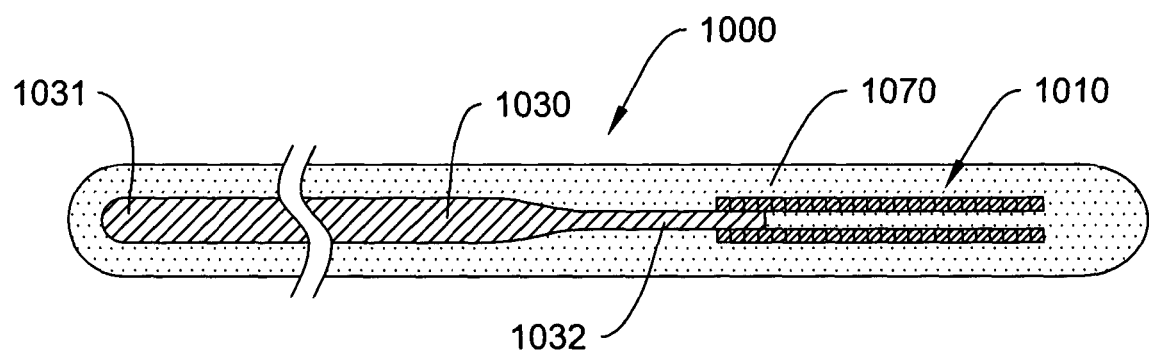
FIG. 10 is a cross-sectional view of an alternative example of a guidewire.

FIG. 10 is a cross-sectional view of the alternative guidewire 1000 with a coil 1010 in accordance with the invention. The coil 1010 is disposed over a portion of the core 1030 and a polymer sheath or sleeve 1070 is disposed over the core 1030 and coil 1010. The coil 1010 is described above.

In this embodiment a polymer tip guidewire 1000 is formed by including the polymer sheath or sleeve 1070 that forms a rounded tip over the coil 1010. The polymer sheath or sleeve 1070 can be made from any material that can provide the desired strength, flexibility or other desired characteristics. The polymer sheath or sleeve 1070 can in some non-limiting embodiments have a length that is in the range of about 2 centimeters to about 300 centimeters and can have an inner diameter that is in the range of about 0.002 inches to about 0.030 inches and an outer diameter that is in the range of about 0.012 inches to about 0.038 inches.

The use of a polymer can serve several functions, such as improving the flexibility properties of the guidewire assembly. Choice of polymers for the sheath or sleeve 1070 will vary the flexibility of the guidewire. For example, polymers with a low durometer or hardness will make a very flexible or floppy tip. Conversely, polymers with a high durometer will make a tip that is stiffer. The use of polymers for the sleeve can also provide a more atraumatic tip for the guidewire. An atraumatic tip is better suited for passing through body passages. Finally, a polymer can act as a binder for radiopaque materials, as discussed in more detail below.

Some suitable materials include polymers, and like material. Examples of suitable polymer material include any of a broad variety of polymers generally known for use as guidewire polymer sleeves. In some embodiments, the polymer material used is a thermoplastic polymer material. Some examples of some suitable materials include polyurethane, elastomeric polyamides, block polyamide/ethers (such as Pebax), silicones, and co-polymers. The sleeve may be a single polymer, multiple layers, or a blend of polymers. By employing careful selection of materials and processing techniques, thermoplastic, solvent soluble and thermosetting variants of these materials can be employed to achieve the desired results.

Further examples of suitable polymeric materials include but are not limited to poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), poly D,L-lactide-co-caprolactone) (PLA/PCL), poly(glycolide-co-caprolactone) (PGA/PCL), polyanhydrides (PAN), poly(ortho esters), poly(phosphate ester), poly (amino acid), poly(hydroxy butyrate), polyacrylate, polyacrylamid, poly(hydroxyethyl methacrylate), polyurethane, polysiloxane and their copolymers.

In some embodiments, the sheath or sleeve 1070, or portions thereof, can include, or be doped with, radiopaque material to make the sheath or sleeve 1070, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the polymer can include different sections having different amounts of loading with radiopaque material. For example, the sheath or sleeve 1070 can include a distal section having a higher level of radiopaque material loading, and a proximal section having a correspondingly lower level of loading.

In some embodiments, it is also contemplated that a separate radiopaque member or a series of radiopaque members, such as radiopaque coils, bands, tubes, or other such structures could be attached to the guidewire core wire 1030, or incorporated into the core wire by plating, drawing, forging, or ion implantation techniques.

The sheath or sleeve 1070 can be disposed around and attached to the guidewire assembly 1000 using any suitable technique for the particular material used. In some embodiments, the sheath or sleeve 1070 can be attached by heating a sleeve of polymer material to a temperature until it is reformed around the guidewire assembly 1000. In some other embodiments, the sheath or sleeve 1070 can be attached using heat shrinking techniques. In other embodiments, the sheath or sleeve 1070 can be co-extruded with the core wire 1030. The sleeve 1070 can be finished, for example, by a centerless grinding or other method, to provide the desired diameter and to provide a smooth outer surface.

Figure 11:
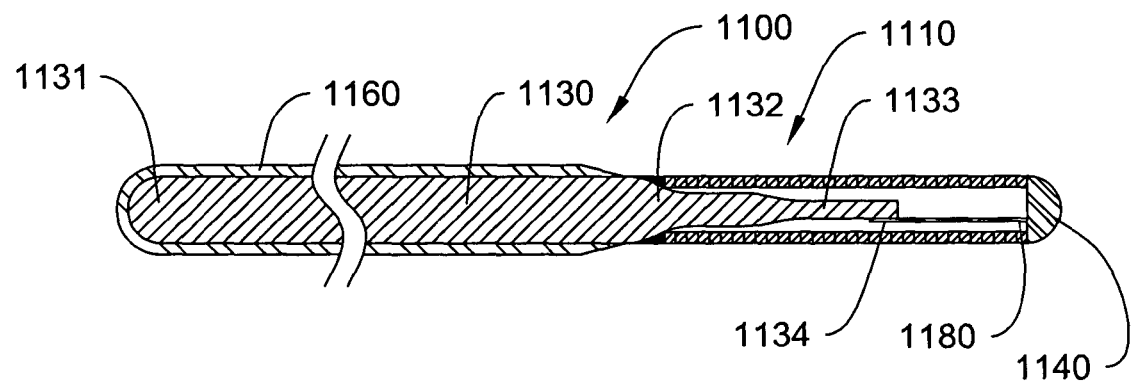
FIG. 11 is a cross-sectional view of an alternative guidewire with a coil.

FIG. 11 is a cross-sectional view of the alternative guidewire 1100 with a coil 1110 in accordance with the invention. The coil 1110 is described above. The guidewire 1100 includes a core 1130. The core may have a proximal section 1131 and an opposing distal section 1132. The distal section 1132 can include a series of taper and constant diameter sections as illustrated in FIG. 11. The coil 1110 can be disposed about a portion of the core distal section 1132. The core 1130 can be formed from a variety of materials as described above. The coil can be disposed between the core 1130 and a distal tip 1140 and constructed as described above. A wire or ribbon 1180 can be disposed between the distal tip 1140 and core 1130.

The wire or ribbon 1180 can be attached adjacent the distal end 1132 of the core 1130, and extend distally to the distal tip 1140. In some embodiments, the wire or ribbon 1180 can be a fabricated or formed wire structure, for example a coiled wire. In the embodiment shown, the ribbon 1180 is a generally straight wire that overlaps with and is attached to the constant diameter region 1133 at attachment point 1134. In some embodiments, the ribbon 1180 overlaps with the constant diameter section 1133 by a length in the range of about 0.05 to 1.0 inch, but in other embodiments, the length of the overlap can be greater or less.

The ribbon 1180 can be made of any suitable material and sized appropriately to give the desired characteristics, such as strength and flexibility characteristics. Some examples of suitable materials include metals, metal alloys, polymers, and the like. In some embodiments, the ribbon 1180 may be formed of a metal or metal alloy such as stainless steel, nickel-chromium alloy, nickel-chromium-iron alloy, cobalt alloy, a nickel-titanium alloy, such as a straightened super elastic or linear elastic alloy (e.g., nickel-titanium) wire. The ribbon 1180 can be attached using any suitable attachment technique. Some examples of attachment techniques include soldering, brazing, welding, adhesive bonding, crimping, or the like. In some embodiments, the ribbon or wire 1180 can function as a shaping structure or a safety structure.

A guidewire 1100 in accordance with sonic embodiments of the invention can optionally include a coating layer 1160 such as a lubricious coating layer over part or all of the guidewire assembly 1100 or even aver part. Hydrophobic coatings such as fluoropolymers provide a dry lubricity which improves guide wire handling and device exchanges. Lubricious coatings improve steer-ability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, the more distal portion 1132 of the guidewire is coated with a hydrophilic polymer and the more proximal portion 1131 is coated 1160 with a fluoropolymer, such as polytetrafluoroethylene (PTFE).

In some other embodiments, a guidewire core wire can have a profile in which the core wire has a greater number of constant diameter sections, separated by a greater number of taper sections. In some embodiments, a guidewire core wire can have fewer or no tapers. The tapers can be as illustrated in FIG. 11, or they can be longer (more gradual), or shorter (less gradual).

One of skill will recognize that a guidewire core wire can have a profile different from that illustrated in FIGS. 9, 10 and 11. For example, the core wire 930, 1030, 1130 can be continuously tapered, can have a tapered section or a number or series of tapered sections of differing diameters, or can have a constant diameter. In some embodiments, core wire 930, 1030, 1130 is tapered or otherwise formed to have a geometry that decreases in cross sectional area toward the distal end thereof. If tapered, core wire 930, 1030, 1130 can include a uniform or a non-uniform transition of the sections, depending on the transition characteristics desired. For example, core wire 930, 1030, 1130 may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness.

Similar to what is described above, the structure used to construct the core wire 930, 1030, 1130 can be designed such that a proximal portion 931, 1031, 1131 is relatively stiff for push-ability and torque-ability, and distal portion 932, 1032, 1132 is relatively flexible by comparison for better lateral track-ability and steer-ability. For example, in some embodiments, a proximal portion 931, 1031, 1131 has a constant or generally uniform diameter along its length to enhance stiffness. However, embodiments including a proximal portion 931, 1031, 1131 having a tapered portion or a series of tapered portions are also contemplated. The diameter of the proximal portion 931, 1031, 1131 can be sized appropriately for the desired stiffness characteristics dependent upon the material used. For example, in some embodiments, a proximal portion 931, 1031, 1131 can have a diameter in the range of about 0.010 to about 0.025 inches or greater, and in some embodiments, in the range of about 0.010 to about 0.018 inches or greater.

A distal portion 932, 1032, 1132 can likewise be constant diameter, can be continuously tapered, or can have a tapered section or a number or a series of tapered sections of differing diameters. In embodiments where the structure of core wire 930, 1030, 1130 is designed such that a distal portion 932, 1032, 1132 is relatively flexible by comparison to the proximal portion 931, 1031, 1131, the distal portion 932, 1032, 1132 can include at least one tapered or reduced diameter portion for better flexibility characteristics.

The lengths of the proximal portions 931, 1031, 1131 and distal portions 932, 1032, 1132 are typically, but not always dictated by the length and flexibility characteristics desired in the final medical device. In some embodiments, the proximal portion 931, 1031, 1131 can have a length in the range of about 50 to about 300 centimeters, and the distal portion 932, 1032, 1132 can have a length in the range of about 3 to about 50 centimeters.

The core wire 930, 1030, 1130 can have a solid cross-section as shown, but in some embodiments, can have a hollow cross-section. In yet other embodiments, core wire 930, 1030, 1130 can include a combination of areas having solid cross-sections and hollow cross sections.

The tapered and constant diameter portions can be formed by any one of a number of different techniques, for example, by centerless grinding, stamping and the like. A centerless grinding technique can utilize an indexing system employing sensors (e.g., optical/reflective, magnetic) to avoid excessive grinding. In addition, the centerless grinding technique can utilize a CBN or diamond abrasive grinding wheel that is well shaped and dressed to avoid grabbing the core wire 930, 1030, 1130 during the grinding process.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. Additionally, alternative tip constructions including a flexible coil tip, a polymer jacket tip, a tip including a coiled safety/shaping wire, or combination thereof, and other such structure may be placed on the guidewire. The scope of the invention is, of course, defined in the language in which the appended claims are expressed.

What is claimed is:

1. A medical device comprising:
    a coil having a longitudinal axis and a radial axis orthogonal to the longitudinal axis, formed from a wire, the wire comprising:
    (a) a cross-section with a centroid;
    (b) a moment of inertia with respect to an axis running through the centroid and parallel to the longitudinal axis of the coil; and
    (c) a moment of inertia with respect to an axis running through the centroid and parallel to the radial axis of the coil, wherein the moment of inertia with respect to an axis running through the centroid and parallel to the longitudinal axis of the coil is greater than the moment of inertia with respect to an axis running through the centroid and parallel to the radial axis of the coil.

2. The medical device according to claim 1, wherein the wire cross-section is a polygonal shape.

3. The medical device according to claim 1, wherein the wire cross-section is a ellipse shape.

4. The medical device according to claim 1, wherein the wire cross-section is an I-Beam shape.

5. The medical device according to claim 1, wherein the wire is formed of a material with a Poisson's ratio from 0.25 to 0.5.

6. The medical device according to claim 1, wherein the coil further comprises a second coil having windings disposed between windings of the coil.

7. The medical device according to claim 1, wherein the wire is a composite wire comprising:
    (a) a cross-section with a centroid, a wire longitudinal axis parallel to the coil longitudinal axis and a wire radial axis parallel to the coil radial axis;
    (b) a first material having a first Young's Modulus at the centroid; and
    (c) a second material having a second Young's Modulus further away from the centroid along the wire radial axis; wherein the second Young's Modulus is greater than the first Young's Modulus.

8. The medical device according to claim 7, wherein the wire cross-section is a circular shape.

9. The medical device according to claim 7, wherein the wire cross-section is a polygonal shape.

10. A medical guidewire comprising:
    (a) an elongated shaft including a proximal region having a first outer diameter and a distal region having a second outer diameter that is smaller than the first outer diameter;
    (b) a coil member connected to the elongated shall at the distal end of the proximal region and extending from the distal end of the proximal region over at least a portion of the distal region, the coil member having an inner diameter that is greater than the second outer diameter, wherein the coil has a longitudinal axis and a radial axis orthogonal to the longitudinal axis, formed from a wire, the wire comprising:
    (i) a cross-section with a centroid;
    (ii) a moment of inertia with respect to an axis running through the centroid and parallel to the longitudinal axis of the coil; and
    (iii) a moment of inertia with respect to an axis running through the centroid and parallel to the radial axis of the coil, wherein the moment of inertia with respect to an axis running through the centroid and parallel to the longitudinal axis of the coil is greater than the moment of inertia with respect to an axis running through the centroid and parallel to the radial axis of the coil.

11. The medical guidewire according to claim 10, wherein the wire cross-section is a polygonal shape.

12. The medical guidewire according to claim 10, wherein the wire cross-section is a ellipse shape.

13. The medical guidewire according to claim 10, wherein the wire cross-section is an I-Beam shape.

14. The medical guidewire according to claim 10, wherein the wire is formed of a material with a Poisson's ratio from 0.25 to 0.5.

15. The medical guidewire according to claim 10, wherein the coil further comprises a second coil having winding disposed between windings of the coil.

16. The medical guidewire according to claim 10, wherein the wire is a composite wire comprising:
    (a) a cross-section with a centroid, a wire longitudinal axis parallel to the coil longitudinal axis and a wire radial axis parallel to the coil radial axis;
    (b) a first material having a first Young's Modulus at the centroid; and
    (c) a second material having a second Young's Modulus further away from the centroid along the wire radial axis; wherein the second Young's Modulus is greater than the first Young's Modulus.

17. The medical device according to claim 16, wherein the wire cross-section is a circular shape.

18. The medical device according to claim 16, wherein the wire cross-section is a polygonal shape.

* * * * *

UNITED STATES PATENT AND TRADEMARK OFFICE
CERTIFICATE OF CORRECTION

PATENT NO. : 7,641,621 B2 Page 1 of 1
APPLICATION NO. : 10/647613
DATED : January 5, 2010
INVENTOR(S) : Crank It is certified that error appears in the above-identified patent and that said Letters Patent is hereby corrected as shown below:

Column 8
Line 17: delete "Weidiogic" and insert therefor -- Weldlogic --.

Column 10
Line 47: delete "crass-section" and insert therefor -- cross-section --.

Column 13
Line 63: delete "sonic" and insert therefor -- some --.
Line 66: delete "aver" and insert therefor -- over --.

Column 16
Line 19: delete "shall" and insert therefor -- shaft --.

Signed and Sealed this

Sixteenth Day of March, 2010

David J. Kappos
*Director of the United States Patent and Trademark Office*